(12) United States Patent
Cirronis et al.

(10) Patent No.: US 9,668,831 B2
(45) Date of Patent: Jun. 6, 2017

(54) DENTAL PROSTHESIS, IN PARTICULAR ON IMPLANTS, OPTIONALLY FOR THE REPLACEMENT OF AN ENTIRE DENTAL ARCH, METHOD AND KIT FOR MAKING IT

(71) Applicant: MICRO.MEDICA S.r.l., Palestro (IT)

(72) Inventors: Giuseppe Cirronis, Palestro (IT); Alessandra Paderno, Palestro (IT)

(73) Assignee: MICRO.MEDICA S.r.l., Palestro (IT)

( * ) Notice: Subject to any disclaimer, the term of this patent is extended or adjusted under 35 U.S.C. 154(b) by 215 days.

(21) Appl. No.: 14/466,534

(22) Filed: Aug. 22, 2014

(65) Prior Publication Data

US 2015/0056572 A1 Feb. 26, 2015

(30) Foreign Application Priority Data

Aug. 23, 2013 (IT) .............................. MI2013A1405

(51) Int. Cl.
*A61C 13/08* (2006.01)
*A61C 8/00* (2006.01)
(Continued)

(52) U.S. Cl.
CPC .......... *A61C 8/0012* (2013.01); *A61C 13/001* (2013.01); *A61C 13/04* (2013.01);
(Continued)

(58) Field of Classification Search
CPC ... A61C 13/0001; A61C 13/003; A61C 13/00; A61C 8/00; A61C 8/0012; A61C 13/081
See application file for complete search history.

(56) References Cited

U.S. PATENT DOCUMENTS 4,906,420 A    3/1990  Brajnovic et al.
5,797,748 A *  8/1998  Reynaud ................ A61C 13/30
                                                      433/220
(Continued)

FOREIGN PATENT DOCUMENTS

EP    0 292 026 A2    11/1988
EP    0 292 026 A3    11/1988
(Continued)

OTHER PUBLICATIONS

Italian Search Report issued on Apr. 15, 2014 in Italian Application No. IT MI 2013 1405 (with English Translation of categories of Cited Documents).
(Continued)

*Primary Examiner* — Jason-Dennis Stewart
(74) *Attorney, Agent, or Firm* — Oblon, McClelland, Maier & Neustadt, L.L.P.

(57) ABSTRACT

The invention concerns a dental prosthesis (1), in particular on implants, for the replacement of an entire dental arch and a method and a kit for making it. The dental prosthesis (1) comprises a structure (2) having a chewing portion (4) which can be substantially in the shape of a tooth or in the shape of a dental arch. The chewing portion (4) develops according to a direction of main development (X) between a contact edge (4a) suitable for engaging the tissues of the patient and a chewing edge (4b) opposite the contact edge (4a). The dental prosthesis (1) further comprises a plurality of hooking elements integrated in the structure (2) and can be engaged in respective endosteal implants applied in the mouth of a patient. The structure (2) is made through a plurality of fibers (5), of the carbon and/or glass and/or graphene type, which develop transverse to the main development (X) of the chewing portion (4), so as to distribute the chewing loads in the same way on the hooking elements (7)

(Continued)

and, consequently, on the endosteal implants provided in the mouth of the patient.

10 Claims, 6 Drawing Sheets

(51) Int. Cl.
    *A61C 13/00*     (2006.01)
    *A61C 13/01*     (2006.01)
    *A61C 13/10*     (2006.01)
    *A61C 13/20*     (2006.01)

(52) U.S. Cl.
    CPC ........ *A61C 13/081* (2013.01); *A61C 13/1003* (2013.01); *A61C 13/206* (2013.01)

(56) References Cited

U.S. PATENT DOCUMENTS

| | | |
|---|---|---|
| 5,846,640 A | 12/1998 | Vallittu |
| 7,758,346 B1 | 7/2010 | Letcher |
| 2009/0240344 A1* | 9/2009 | Colvin ................. A61F 2/80 623/36 |

FOREIGN PATENT DOCUMENTS

| | | |
|---|---|---|
| FR | 2 815 352 A1 | 4/2002 |
| WO | WO 96/25911 | 8/1996 |
| WO | WO 02/100355 A1 | 12/2002 |
| WO | WO 2005/055862 A1 | 6/2005 |

OTHER PUBLICATIONS

Italian Search Report issued Apr. 15, 2014 in Italian Application MI 2013 001405, filed on Aug. 23, 2013 ( with English Translation of categories of Cited Documents).

* cited by examiner

DENTAL PROSTHESIS, IN PARTICULAR ON IMPLANTS, OPTIONALLY FOR THE REPLACEMENT OF AN ENTIRE DENTAL ARCH, METHOD AND KIT FOR MAKING IT

The present invention refers to a dental prosthesis, in particular on implants, optionally for the replacement of an entire dental arch.

The present invention, furthermore, refers to a method for obtaining a dental prosthesis, in particular on implants, optionally for the replacement of an entire dental arch.

Another object of the present invention is a kit for obtaining a dental prosthesis, in particular on implants, optionally for the replacement of an entire dental arch.

The present invention is suitable for being used in the field of dentistry and, in particular, it refers to dental prostheses that are intended for the partial and/or total replacement of natural dental arches of patients.

As it is known, dental prostheses are products, which are made in dentistry to replace lost or compromised original sets of teeth. Among the various dental prostheses that can be made total dental prostheses are provided, which discharge the chewing loads on the mucosa and/or on the bone beneath and the task of which is to entirely re-establish the chewing functions of the patient.

Normally, making total prostheses is carried out by using respective suitably prepared models. With such models it is possible to obtain a sub-structure that is generally made of metal, on which the aesthetic part that reproduces the teeth of the patient is obtained as faithfully as possible.

The aforementioned metal sub-structures are made so as to enclose the turrets and/or similar hooking elements in the supporting endosteal implants that are applied to the mandible and/or jaw bone tissue of the patient, allowing it to be stably fixed.

Although it is widespread to make sub-structures in metal material when making total dental prostheses, the Applicant has found that making and using metal sub-structures, has drawbacks and can be improved in different aspects, mainly relating to the transmission of the chewing loads on the support endosteal implants, to the overall mass of the prosthesis made, as well as to the speed, ease and rapidity of making them.

In particular, the Applicant has found that the metal sub-structures are not capable of equally distributing the chewing loads on the endosteal support implants provided in the mouths of the patients, with the risk of damaging such implants and/or tearing the tissues of the patients on which they are anchored.

In addition, the metal sub-structures transmit, during chewing, the chewing loads directly on the support endosteal implants, in a way that is identical to how they receive them. Therefore, the endosteal implants are considerably stressed during chewing with unpleasant consequences in terms of structural integrity and its configuration.

The metal sub-structures are not therefore capable of absorbing in any way even a part of the chewing loads that are generated during chewing.

It should be furthermore noted that using metal considerably makes dental prostheses heavier, the overall mass of which can be appreciated directly by the patient whom it is applied to.

The high mass of dental prostheses with metal sub-structures, the overall weight of which can vary from 35 grams to 40 grams, makes the patient tired quickly when chewing food products.

In addition, it is not possible to make the aforementioned metal sub-structures rapidly and they require the dental technician involved to be highly experienced and competent.

The main purpose of the present invention is to provide a dental prosthesis, in particular on implants, optionally for the replacement of an entire dental arch, a method and a kit for making it, that is capable of solving the problems of the prior art.

One purpose of the present invention is to provide a dental prosthesis that is highly resistant.

A further purpose of the present invention is to propose a dental prosthesis that is considerably light.

One purpose of the present invention is to provide a dental prosthesis the structure of which is capable of equally distributing the chewing loads on the endosteal implants of the patient.

A further purpose of the present invention is to propose a dental prosthesis the structure of which is capable of absorbing and/or damping a part of the chewing load that is generated when chewing.

Another purpose of the present invention is to provide a dental prosthesis that is easy to make.

A further purpose of the present invention is to propose a dental prosthesis that can be made quickly.

Another purpose of the present invention is to provide a dental prosthesis that does not require the dental technician to be highly experienced.

The purposes specified above, and others, are substantially achieved with a dental prosthesis, in particular on implants, optionally for the replacement of an entire dental arch, a method and a kit for making it, as expressed and described in the following claims.

We shall now describe, as an example, a preferred but not exclusive embodiment of a dental prosthesis, in particular on implants, optionally for the replacement of an entire dental arch, a method and a kit for making it, in accordance with the present invention.

The description shall be made in the rest of the description with reference to the attached drawings, given purely as an indication and therefore not for limiting purposes, in which.

Figure 1:
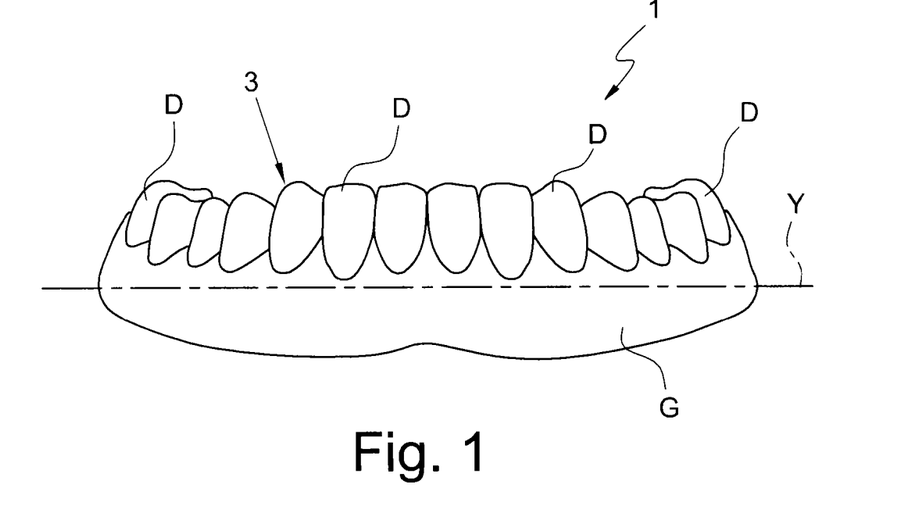
FIG. 1 is a schematic view of a dental prosthesis, in particular on implants, optionally for the replacement of an entire dental arch, in accordance with the present invention.

With reference to FIG. 1, number 1 wholly indicates a dental prosthesis, in particular on implants, optionally for the replacement of an entire dental arch, in accordance with the present invention.

The dental prosthesis 1, represented in FIG. 1, comprises a plurality of teeth D that are arranged side by side to each other along an arched development that reproduces the natural curvature of the dental arch of a patient and a gingival portion G that is engaged with the teeth D along an edge of the dental prosthesis 1 itself.

Figure 2:
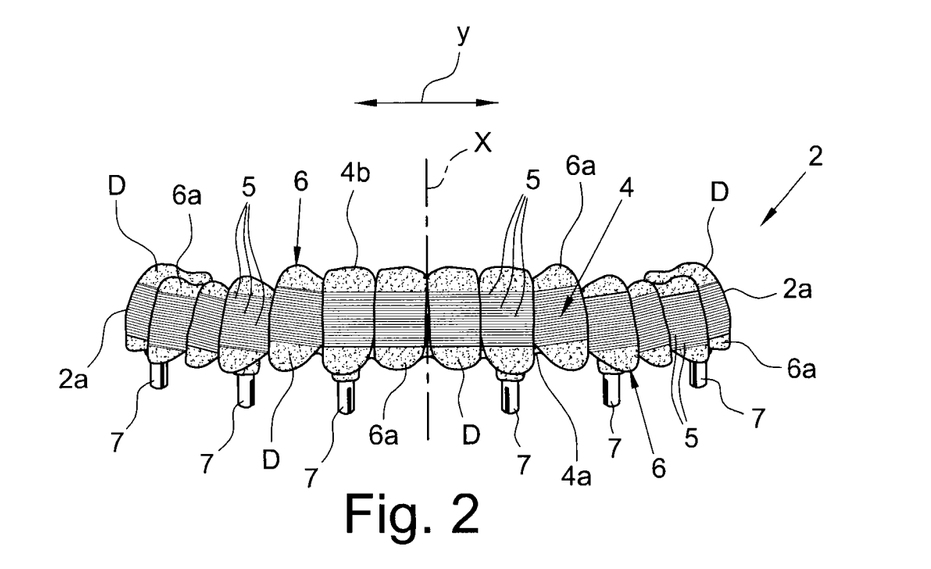
FIG. 2 is a schematic view of a load-bearing structure of the prosthesis according to FIG. 1.

As visible in FIG. 2, the dental prosthesis 1 comprises a load-bearing structure 2 that is suitable for supporting the aesthetic part 3 (FIG. 1) that is made on it.

The structure 2 mainly extends along a direction Y (FIGS. 1, 2, 8 and 12), advantageously according to a substantially arched development, and has at least one chewing portion 4 that develops transverse with respect to the structure 2.

According to one advantageous aspect of the present invention, the chewing portion 4 is made in a single piece with the structure 2 and substantially has the shape of a tooth or of a dental arch.

In detail, by chewing portion 4, we mean the part of structure 2 that extends according to a direction of main development X (FIG. 2) between a contact edge 4a, which is suitable for engaging the tissues of the patient, and a chewing edge 4b, which is opposite the contact edge 4a, which is intended for chewing food products.

Preferably, the chewing portion 4 of the structure 2 reproduces, for each tooth D, an entire dental arch of the patient.

According to one advantageous aspect of the present invention, the structure 2 is obtained by using a plurality of fibres 5 (FIG. 2), optionally carbon fibres and/or glass fibres, which are suitably impregnated with a suitable thermosetting resin 5a.

Advantageously, the fibres 5 used can be graphene fibres, preferably in the form of agglomerate sheets of particles of graphene.

Preferably, the agglomerate sheets of graphene have an average thickness of between 10 nm and 200 nm (nanometers).

Alternatively it is possible for even single particles of graphene to be used, preferably having an average thickness of between 2 nm and 20 nm (nanometers).

The graphene fibres 5 and/or the particles of graphene can be used individually, or in combination with carbon fibres 5 and/or fibre glass 5, according to the contingent requirements.

As visible in FIG. 2, the fibres 5 extend along the direction of development Y of the structure 2 advantageously transverse with respect to the main direction of development X of the chewing portion 4. In detail, the fibres 5 of the structure 2 extend unidirectionally transverse with respect to the teeth D of the chewing portion 4 defined by the latter, following the curvature and the arched development of the dental arch to be reproduced.

In particular, the fibres 5 are advantageously superimposed and/or adjacent one another, from one end 2a to the other of the structure 2, developing, transverse with respect to the main development direction X of the chewing portion 4, which is substantially parallel with respect to one another.

It should not however be excluded that the fibres 5 which the structure 2 is made of can be interlaced.

Also in this situation, the orientation of the fibres 5 remains transverse with respect to the chewing portion 4 despite of the fact that they cross one another along the longitudinal development Y of the structure 2.

Advantageously, the carbon fibres used for making the structure 2 have a flexural modulus of between, 250.000 Mpa and 450.000 Mpa.

In the case in which fibre glass is used to make the structure 2, the elastic modulus of the latter is of between 70.000 Mpa and 110.000 Mpa.

Preferably, both the chewing edge 4b and the contact edge 4a of the chewing portion 4 of the structure 2 are made by at least one filler thermosetting resin 6 (FIG. 2), which is optionally filled with micro-particles 6a, in particular of a length comprised between 10 μm and 6 mm, preferably between 15 μm and 25 μm, even more preferably between 18 μm and 22 μm, obtained from the chopping of the fibres 5 that can be used for obtaining the structure 2, and/or filled with graphene particles.

The average thickness of the graphene particles is advantageously of between 2 nm and 20 nm (nanometers).

Advantageously, the thermosetting resins that can be used to obtain the structure 2 of the dental prosthesis 1 can comprise epoxy resins, vinyl ester, polyester and acrylic resins. It should however be noted that the use of other resins and/or of similar aggregating substances that are capable of carrying out the same tasks can be contemplated for the purposes of the invention.

Again with reference to FIG. 2, the structure 2 comprises at least one hooking element 7, preferably a plurality of hooking elements 7, engaged, in particular integrated, in the structure 2 itself and engageable to respective endosteal implants (which are not represented because they are of the known type) applied inside the mouth of a patient for fixing the dental prosthesis 1 to the tissues of the patient.

In detail, each hooking element 7 comprises a respective turret that is substantially cylindrical for fixing the dental prosthesis 1 to the endosteal implants of the patient.

Advantageously, each hooking element 7 develops, at least partially, inside the chewing portion 4 along the main development direction X of the latter, transverse with respect to the fibres 5 that form the structure 2.

The structure 2 of the dental prosthesis 1 is made according to a method that provides a mould 100 (FIGS. 3, 4, 7 and 9) that is provided with at least one hooking element 7, preferably a plurality of hooking elements 7, which are suitable for engaging respective endosteal implants that are applied into the mouth of a patient and for fixing the prosthesis to the tissues of the latter, and the provision of a counter-mould 101 (FIGS. 6 to 8) in which at least one molding cavity 101a is defined, having, in negative, the shape of the structure 2 or of a chewing portion 4 of the dental arch of the patient to be reproduced or the shape of the entire dental arch thereof.

Figure 3:
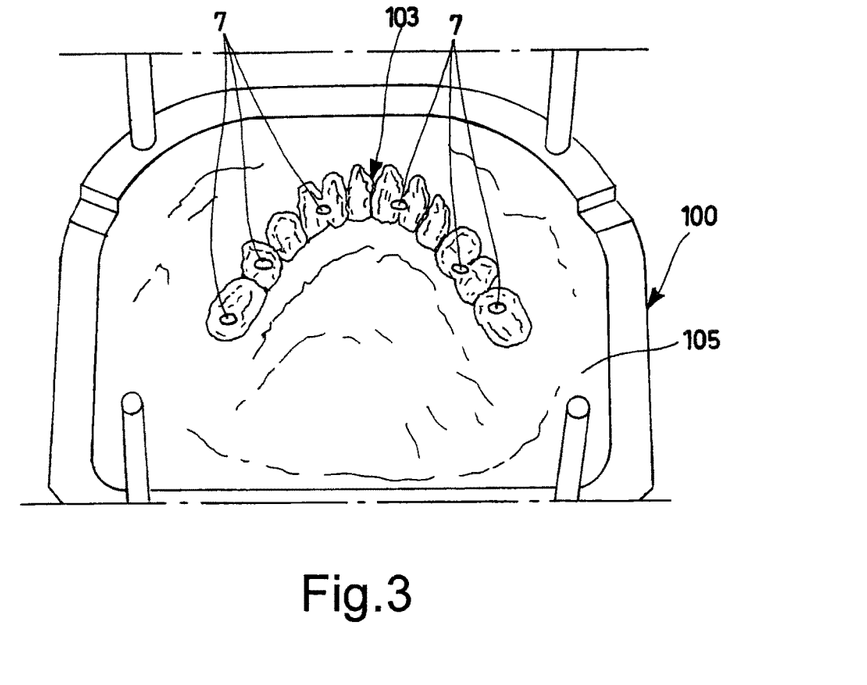
FIG. 3 is a schematic representation of a mould that is provided with a model of a dental arch to be made.
Figure 4:
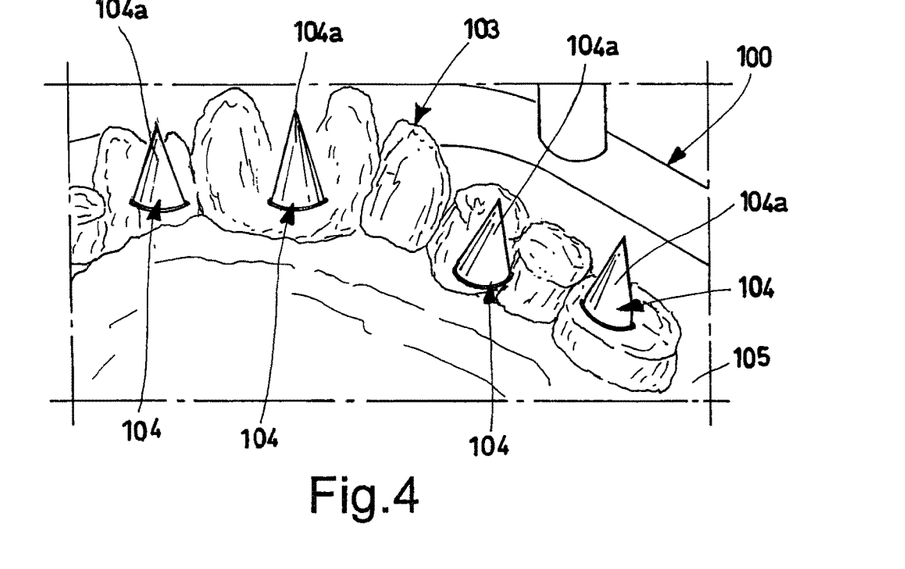
FIG. 4 is a schematic representation of the mould according to FIG. 3, in which the additional elements with a conical portion are applied to the hooking elements of the model carried by the mould.
Figure 7:
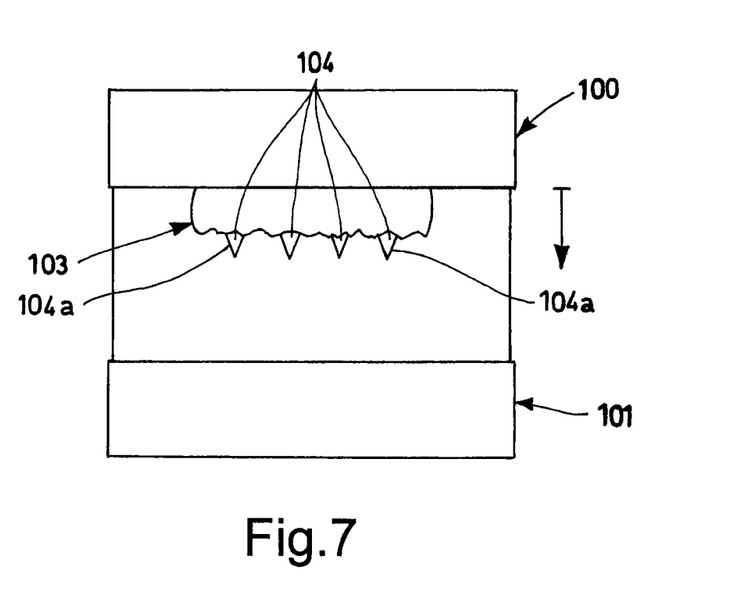
FIG. 7 is a representation of the coupling between the mould provided with a model according to FIGS. 3 and 4, and a counter-mould according to FIG. 6.

As illustrated in FIGS. 3, 4 and 7, the provision of the mould 100 is provided by making a model 103, in positive, of the dental arch of the patient to be reproduced, said model 103 being provided with hooking elements 7 on which respective additional elements 104 are engaged, preferably made in silicone and/or in a similar material, and each having at least one respective sharp-pointed portion 104a, optionally conical or wedge-shaped, projecting from the model 103 itself.

Figure 6:
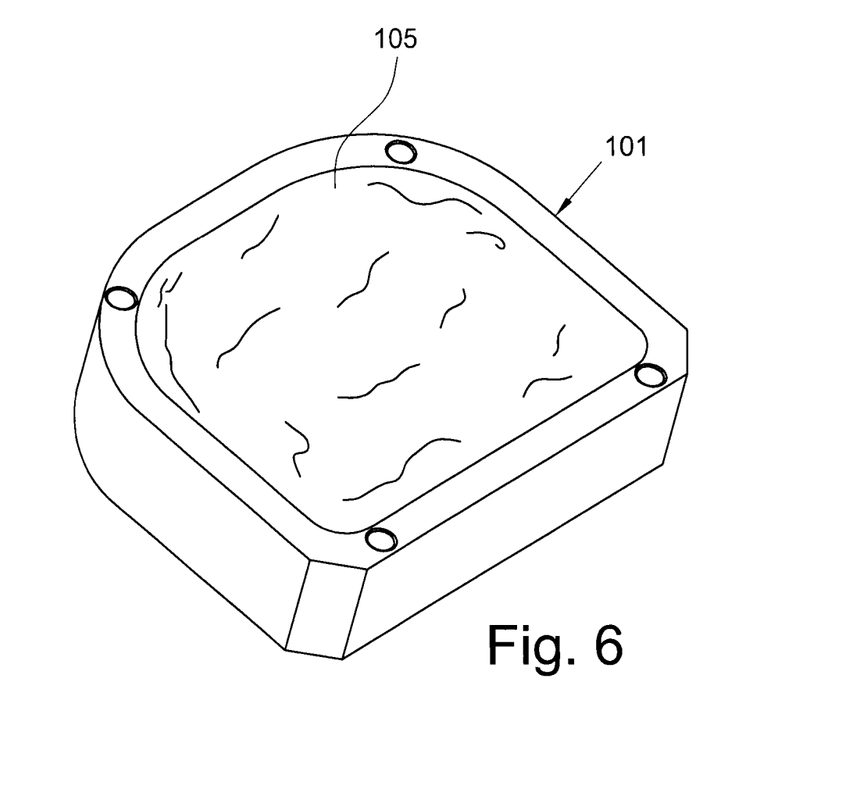
FIG. 6 is a perspective schematic representation of a counter-mould that is filled with a deformable substance that is used in dentistry.

The provision of the counter-mould 101 is carried out by filling the latter with a deformable material 105, preferably silicone for dentistry, and by coupling on it the mould 100 carrying the model 103 that is prepared beforehand with the hooking elements and the additional elements 104.

The coupling between the mould 100 and counter-mould 101 determines the formation, in the deformable material 105, of the aforementioned molding cavity 101a (FIG. 8) that reproduces in negative the shape of the chewing portion 4 or of the entire set of teeth of the patient to be reproduced, corresponding to the model 103 provided with hooking elements 7 and with additional elements 104.

Figure 8:
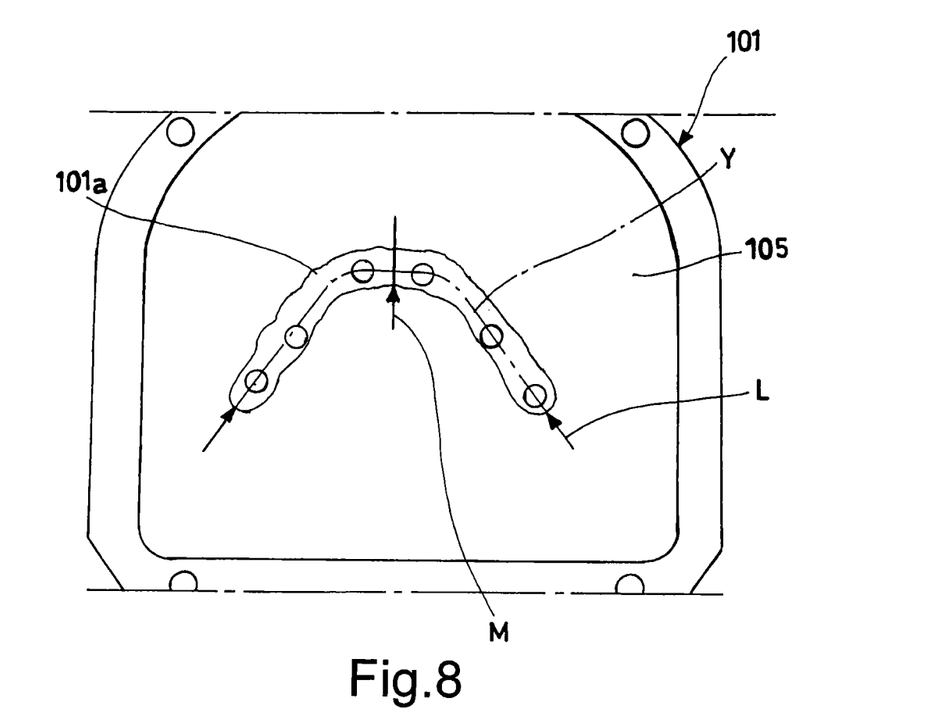
FIG. 8 is a schematic representation of the counter-mould according to FIGS. 6 and 7, after making a molding cavity.
Figure 11:
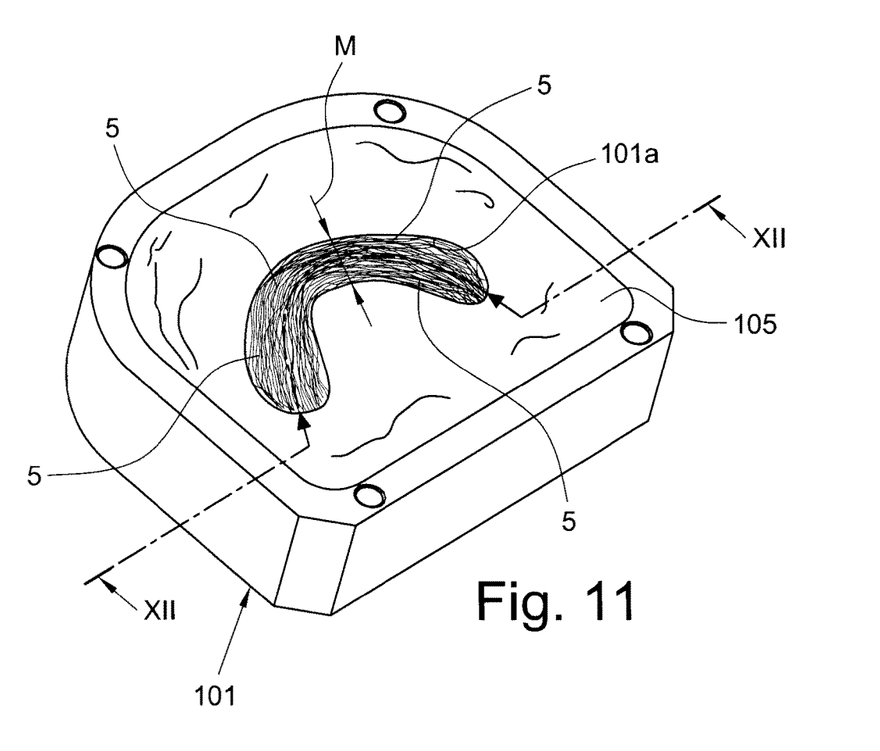
FIG. 11 is a schematic representation of the counter-mould according to FIGS. 6 to 8, which is filled with a plurality of fibres that are impregnated with a thermosetting resin.
Figure 12:
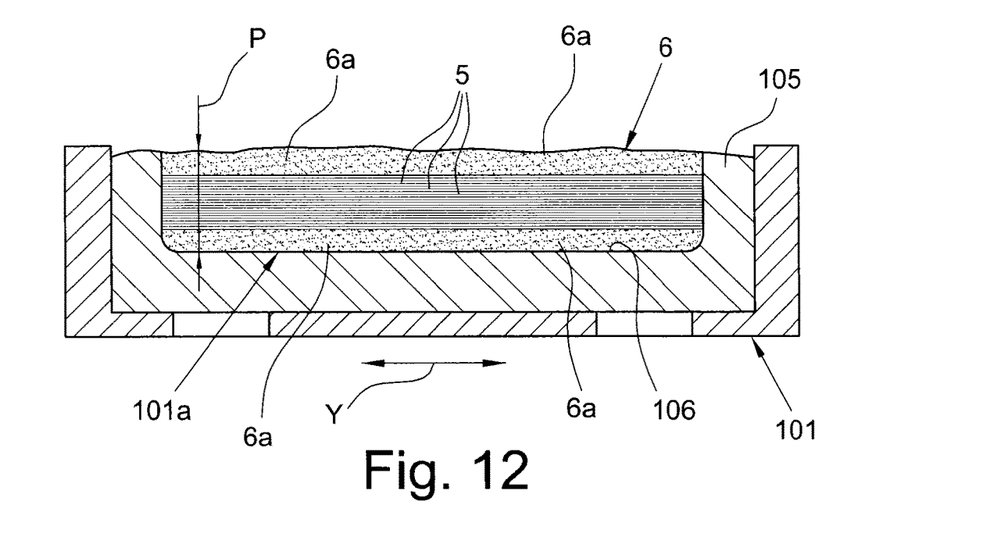
FIG. 12 is a schematic section view of the counter-mould carried out according to the line XII-XII of FIG. 11.

As visible in FIGS. 8, 11 and 12, the molding cavity 101a has: a relative depth P (FIG. 12) that is substantially at the height of the corresponding structure 2 and/or chewing portion 4 to be formed; a width M (FIGS. 8 and 11), relative to the thickness of the corresponding structure 2 and/or chewing portion 4 to be formed; and, a length L (FIG. 8), relative to the amplitude of the corresponding structure 2 and/or chewing portion 4 to be made. Of course, the dimensions of the molding cavity 101a vary in function of the shape of the dental arch to be reproduced.

Subsequently to making the molding cavity 101a, the mould 100 is separated from the counter-mould 101. The additional elements 104 are removed from the model 103 engaged in the mould 100, so as to free the hooking elements 7 and to allow them to be released from the mould 100.

Once the hooking elements 7 have been released from the mould 100, it is possible to remove the model 103.

Advantageously, the hooking elements 7 are removed from the model 103, so as to be located again in the mould 100 according to the same initial position. The arrangement of the hooking elements 7 is facilitated by the presence of a base (which is not illustrated being of the known type) which is inserted into the mould 100 and is almost totally covered with a deformable material 105 (FIGS. 3, 4 and 9), preferably silicone for dentistry, during its provision.

In detail, the hooking elements 7 are positioned at an auxiliary forming cavity 106 which is defined in the mould 100, to complete the molding cavity 101a of the counter-mould 101, after coupling the mould 100 with the counter-mould 101.

Figure 9:
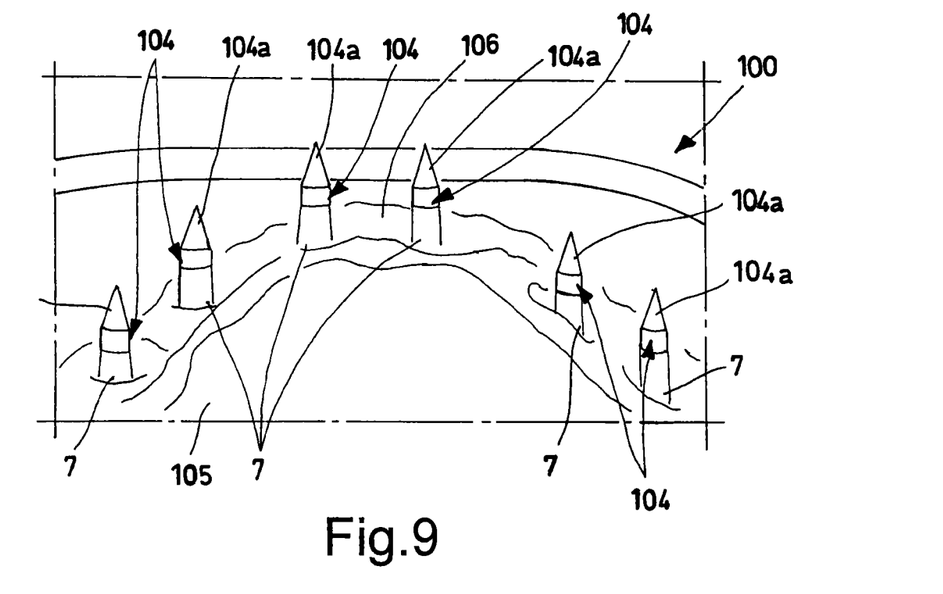
FIG. 9 is a schematic representation of the mould according to FIGS. 3, 4 and 7, after removing the model and the repositioning of some components of the structure of the dental prosthesis.

Once the hooking elements 7 have been fixed in the provided position inside the mould 100, the additional elements 104 are applied onto the hooking elements 7, as illustrated in FIG. 9.

Figure 5:
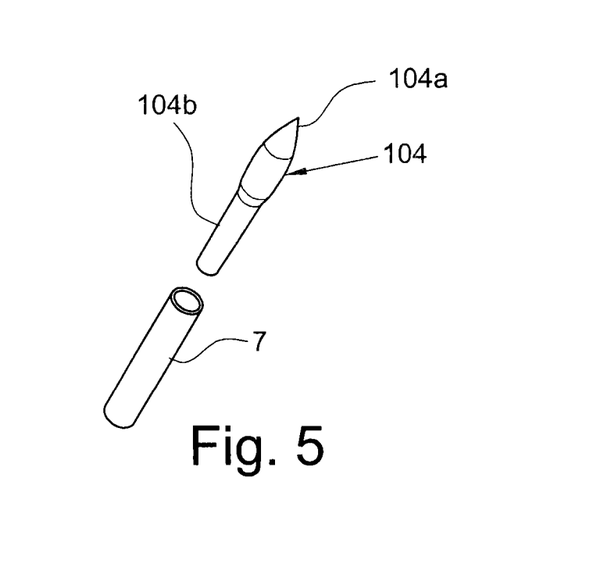
FIG. 5 is a perspective schematic representation in an exploded view of a hooking element and of a respective additional element that can be used for obtaining the prosthesis according to the present invention.

In detail, such an operation is carried out by inserting the stem 104b (FIG. 5) of each additional element 104 into the respective hooking element 7 and fixing them by means of glueing elements or similar joining substances.

The repositioning of the hooking elements 7 with the respective additional elements 104 determines the end of the provision of the mould 100.

Figure 10:
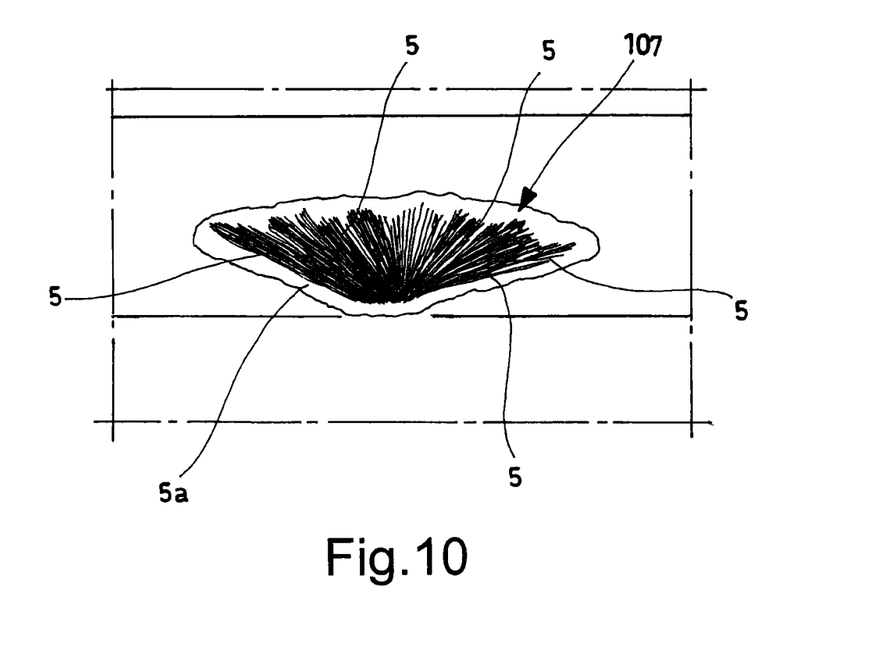
FIG. 10 is a schematic representation of the application of a thermosetting resin on a bundle of fibres.

Subsequently, at least one plurality of fibres 5, advantageously in the form of one or more bundles 107 (FIG. 10), is impregnated with a thermosetting resin 5a.

Once they have been impregnated with the aforementioned thermosetting resin 5a, the plurality of fibres 5 is arranged, at least partially, preferably entirely, into the molding cavity 101a of the counter-mould 101 (FIG. 11) according to an orientation that is transverse with respect to the depth P (FIG. 12) and to the width M (FIGS. 8 and 11) of the latter.

The impregnation of the fibres 5 with the suitable thermosetting resin 5a and the arrangement thereof into the molding cavity 101a of the counter-mould 101, are reiterated until a predetermined filling level has been reached, preferably until the same molding cavity 101a has been completely filled.

In order to detect the details of the molding cavity 101a of the counter-mould 101 while at the same time strengthening the chewing edge 4b of the structure 2 being formed, a filler thermosetting resin 6 that is filled with micro particles 6a that are obtained from the chopping of the fibres 5 which can be used for obtaining the structure 2 of the dental prosthesis 1 being formed, is suitably provided and applied into the molding cavity 101a of the counter-mould 101, before the plurality of previously impregnated fibres 5 are inserted into the latter.

In detail, as visible in the schematic section view of FIG. 12, the application of the filler thermosetting resin 6 is carried out on the bottom of the molding cavity 101a of the counter-mould 101 so as to faithfully reproduce the shape of the chewing edge 4b of the chewing portion 4.

Once the molding cavity 101a of the counter-mould 101 has been filled with the fibres 5, a predetermined amount of filler thermosetting resin 6 is then applied onto them, so as to define a covering layer (FIG. 12) that is adapted to be pressed by the mould 100 during the engagement of the latter on the counter-mould 101.

Once the covering layer in filler thermosetting resin 6 has been applied, the mould 100 is again fixedly engaged to the counter-mould 101. In such a way, the hooking elements 7, together with the additional elements 104, are inserted into the molding cavity 101a of the counter-mould 101 between the fibres 5, in a transverse manner with respect to the latter.

While closing the mould 100 on the counter-mould 101, the sharp-pointed portions 104a of the additional elements 104 are inserted into the molding cavity 101a of the counter-mould 101 between the fibres 5 without damaging them and facilitating the insertion of the hooking elements 7.

The advantageous formation of an upper layer of filler thermosetting resin 6 provided with micro particles 6a produces the effect, during the coupling between the mould 100 and the counter-mould 101, of eliminating possible air bubbles that can be formed during the impregnation step of the fibres 5. In detail, the upper layer of filler thermosetting resin 6, operates, upon mutual pressure of the mould 100 and of the counter-mould 101, like a press, pressing the fibres 5 transversally against the bottom of the molding cavity 101a of the counter-mould 100. Such a pressure action, in addition to setting at best the fibres 5 in the molding cavity 101a, causes the breakage of all of the air bubbles possibly present inside such a cavity 101a.

Once the mould has been locked, the hardening of the thermosetting resins 5a, 6 occurs by means of suitable known heating means, so as to make a respective solid structure 2, on which the chewing portion 4 is defined.

Once the hardening step has ended, the structure 2 is extracted from the mould 100 and from the counter-mould 101, so as to, subsequently, finish it off according to the construction of the final aesthetic part to be made.

The dental prosthesis 1 mentioned above, which is obtained by means of the method described, solves the problems of the prior art and obtains important advantages.

Firstly, the transverse arrangement of the fibres with respect to the hooking elements and, consequently, to the endosteal implants that are applied into the mouth of the patients, as well as the main development direction of the chewing portion and therefore the main chewing direction of the patients, permits an optimal arrangement of the chewing loads on the hooking elements themselves.

In particular, the arrangement of bundles of fibres that develop unidirectionally transverse with respect to the teeth obtained, allows to evenly distribute the chewing loads on the endosteal implants provided in the mouths of the patients.

Moreover, the transverse orientation of the aforementioned fibres gives the structure obtained a slight flexibility which allows it to absorb and/or partially dampen the aforementioned chewing loads thus reducing the stresses on the hooking elements and on the endosteal implants of the patients.

It is also worth mentioning that the use of carbon fibres and/or of fibre glass and/or graphene fibre allows to considerably reduce the overall mass of the dental prosthesis produced, the lightness of which allows to tire the patient less during chewing.

Indeed, a structure in carbon fibre can weigh about 3 or 4 grams, thus being considerably lower than the 35 or 40 grams of metal structures used for making known prostheses.

It is also worth noting that the use of carbon fibres and/or graphene fibres provides the dental prosthesis with high resistance.

In addition, the method for making the aforementioned dental prosthesis is simple and easy to make even by not particularly experienced dental technicians.

It is also worth considering that the method described can be carried out rapidly since the arrangement of the fibre bundles in the molding cavity of the counter-mould only requires the fibres to be impregnated with the thermosetting resin and to be subsequently inserted into the molding cavity.

The invention claimed is:

1. A dental prosthesis comprising:
   a structure mainly extending along a direction and having at least one chewing portion developing transverse to said structure; and
   at least one hooking element engaged in said structure and engageable to a respective implant applied in the mouth of a patient for fixing said dental prosthesis to tissues of the latter,
   wherein said structure is made through a plurality of carbon fibres and/or glass fibres, developing along the development of said structure transverse to the development of the chewing portion,
   wherein said chewing portion is made in a single piece with said structure and is substantially tooth or dental-arch shaped, said chewing portion developing according to a direction of main development between a contact edge suitable for engaging the tissues of the patient and a chewing edge opposite said contact edge, said chewing and/or contact edges being made through a filler thermosetting resin which is filled with micro particles of fibre.

2. The dental prosthesis according to claim 1, wherein the main development of said structure is substantially arched, said fibres being unidirectional and developing, transverse to the development of said chewing portion, substantially along the arched development of said structure.

3. The dental prosthesis according to claim 1, wherein said fibres are superimposed and/or adjacent transversally to the development of the chewing portion of said structure and along the arched development of said structure.

4. The dental prosthesis according to claim 1 wherein said structure comprises at least one layer made through at least one filler thermosetting resin, of length comprised between 10 μm and 6 mm, obtained from the chopping of the fibres usable for obtaining said structure.

5. The dental prosthesis according to claim 4, wherein the length is between 15 μm and 25 μm.

6. The dental prosthesis according to claim 1, wherein each hooking element develops, at least partially, within said structure, said fibres being arranged transverse with respect to each hooking element provided.

7. The dental prosthesis according to claim 1, wherein at least one part of said fibres of said structure of said dental prosthesis is made of graphene, in the form of agglomerate sheets of particles of graphene and/or through single particles of graphene, in combination with said carbon fibres and/or said glass fibres.

8. A kit for making a dental prosthesis according to claim 1, comprising:
   a plurality of carbon fibres and/or glass fibres, in the form of bundles, and/or graphene fibres, in the form of agglomerate sheets of graphene particles and/or single particles of graphene;
   at least one thermosetting resin for impregnating said fibres;
   at least one filler thermosetting resin of length comprised between 10 μm and 6 mm, obtained from the chopping of the same fibres, said filler thermosetting resin being usable before and after the insertion of said plurality of impregnated fibres into respective cavity of a mould and a counter-mould for detecting the details of such cavities.

9. The kit according to claim 8, wherein the length is between 15 μm and 25 μm.

10. The dental prosthesis according to claim 1, wherein the dental prosthesis replaces an entire dental arch.

\* \* \* \* \*